United States Patent [19]

Tiep

[11] 4,422,456
[45] Dec. 27, 1983

[54] NASAL CANNULA STRUCTURE

[75] Inventor: Brian L. Tiep, Monrovia, Calif.

[73] Assignee: City of Hope National Medical Center, Duarte, Calif.

[21] Appl. No.: 299,873

[22] Filed: Sep. 8, 1981

[51] Int. Cl.³ .............................................. A61M 15/08
[52] U.S. Cl. .......................... 128/207.18; 128/207.17; 604/94
[58] Field of Search ...................... 128/200.26, 205.25, 128/206.21, 207.13, 207.17, 207.18, 203.22, DIG. 26; 604/94

[56] References Cited

U.S. PATENT DOCUMENTS

| 2,763,263 | 9/1956 | Ellman | 128/203.22 |
| 4,156,426 | 5/1979 | Gold | 128/207.18 |
| 4,221,217 | 9/1980 | Amezcua | 128/203.22 |

FOREIGN PATENT DOCUMENTS 667077 7/1963 Canada ............................ 128/207.18

Primary Examiner—Kyle L. Howell
Assistant Examiner—Harry J. Macey
Attorney, Agent, or Firm—Edward D. O'Brian; K. H. Boswell

[57] ABSTRACT

A nasal cannula structure capable of being adjusted so as to fit comfortably relative to the nose of a user can be constructed so as to utilize an elongated tubular conduit held by a suitable support so that a portion of the conduit extends beneath and adjacent to the nostrils of the nose of the user. Two separate, spaced holes are provided in this portion of the conduit. Each of these holes is covered by a sleeve which fits closely around the exterior of the conduit in such a manner there is no gas leakage between the exterior of the conduit and the interiors of the sleeves and in such a manner that the positions of the sleeves relative to the conduit can be changed. These sleeves carry small tubes which are in communication with the holes in the conduit and which also extend into the nostrils of a user.

7 Claims, 5 Drawing Figures

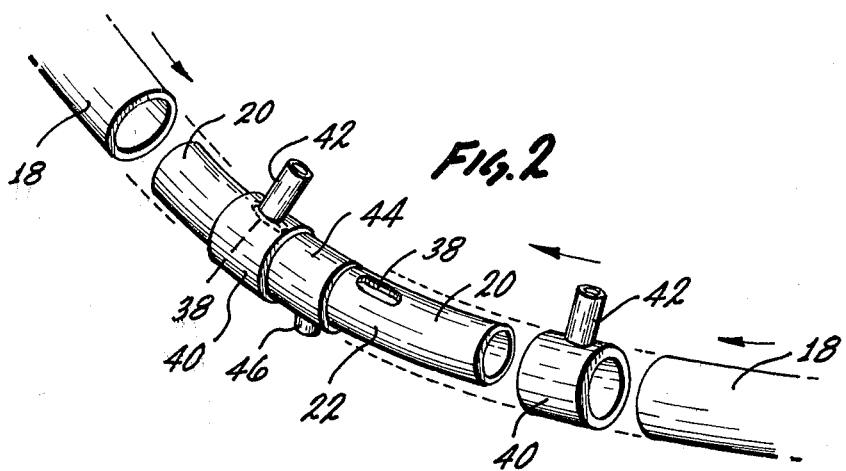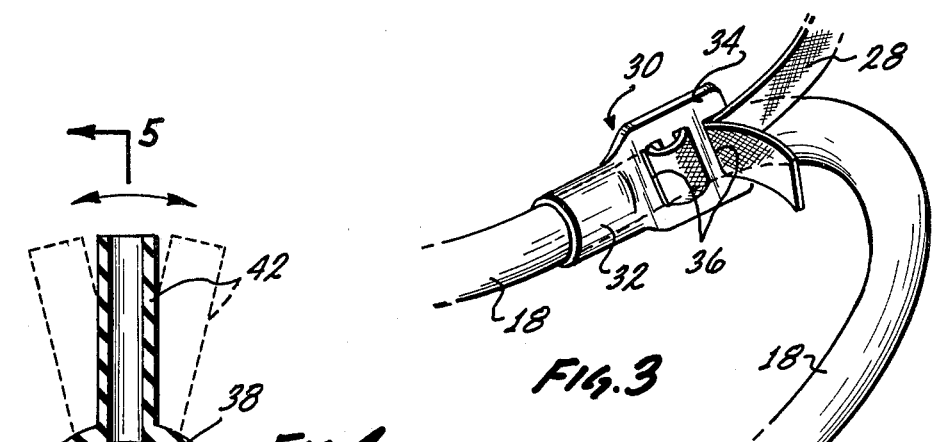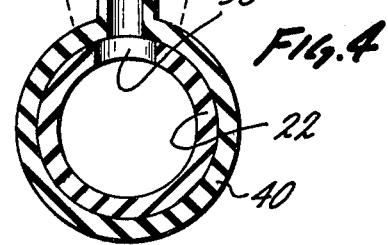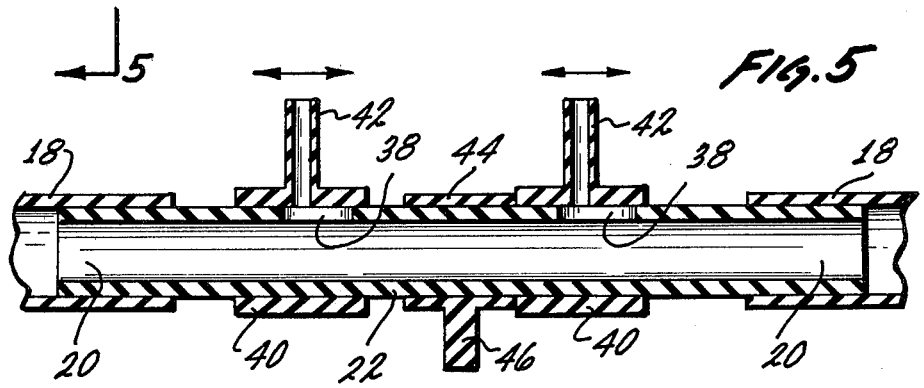

NASAL CANNULA STRUCTURE

BACKGROUND OF THE INVENTION

The invention set forth in this specification relates to new and improved nasal cannulas.

An understanding of the present invention does not require an understanding of the various medical uses of a nasal cannula. These structures are normally utilized in conveying a gas or a gas mixture to or from the nostrils of the individual as part of a treatment procedure. Although a nasal cannula can be used so that substantially all flow to or from the nostrils of an individual is through such cannula, such nasal cannula are normally utilized so that only a part of the gas flow from or to the nostrils goes through the cannula.

Because of the importance of the nasal cannula in many medical procedures, it is quite important that these cannula fit with respect to the nose of a user in such a manner that there is substantially no chance of the cannula becoming closed off or knocked out of an operative position as the result of normal movement or the like. Further, it is quite important that the cannula be constructed in such a manner as to be relatively comfortable for an individual to use. Such cannula have often been held relative to the nose through the use of adhesive tape or the like. Such expedients are considered to be relative undesirable because of the way they feel to a user. They are also somewhat undesirable because of the relative difficulty involved in locating and removing these cannula.

SUMMARY OF THE INVENTION

A broad objective of the present invention is to provide a new and improved nasal cannula, and in particular, a cannula which will not be closed off or knocked from an operative position when used. The invention is intended to provide nasal cannulas which can be easily and conveniently located in an operative positon and which can be removed from the face of a user just as conveniently. The invention is also intended to provide nasal cannulas which are particularly desirable because they are relatively comfortable to an individual user.

In accordance with this invention, these and various related objectives as will be apparent from a consideration of this specification are achieved by providing a nasal cannula structure utilizing an elongated tubular conduit in which the improvement comprises: support means for supporting said conduit so that a portion of said conduit extends beneath and adjacent to the nostrils of the nose of a user, two separate, spaced holes located in said portion of said conduit said holes being separated from one another by an amount approximately corresponding to the spacing between the nostrils of the nose of a user, two separate sleeves located around said portion of said conduit, each of said sleeves covering one of said holes, a tube capable of fitting into a nostril of a user attached to each of said sleeves so as to extend outwardly from it, said sleeves fitting closely against the exterior of said conduit so as to prevent gas leakage between the exterior of said conduit and the interiors of said sleeves, said sleeves also fitting against the exterior of said conduit in such a manner as to permit the relative locations of said sleeves with respect to said conduit to be adjusted so that said tubes fit within the nostrils of the nose of the user when said tubes are in communication with said holes.

BRIEF DESCRIPTION OF THE DRAWINGS

Because of the nature of this invention, it is preferably explained to a greater extent than in the preceding summary by referring to the accompanying drawings in which:

FIG. 2 is a partially exploded isometric view showing the principal, operative parts of the cannula structure illustrated in the preceding figure;

FIG. 3 is an isometric view showing a part of a support means for holding the remainder of the cannula structure in place;

FIG. 4 is a partial cross-sectional view taken at line 4—4 of FIG. 1; and

FIG. 5 is a partial cross-sectional view taken at line 5—5 of FIG. 4.

Figure 1:
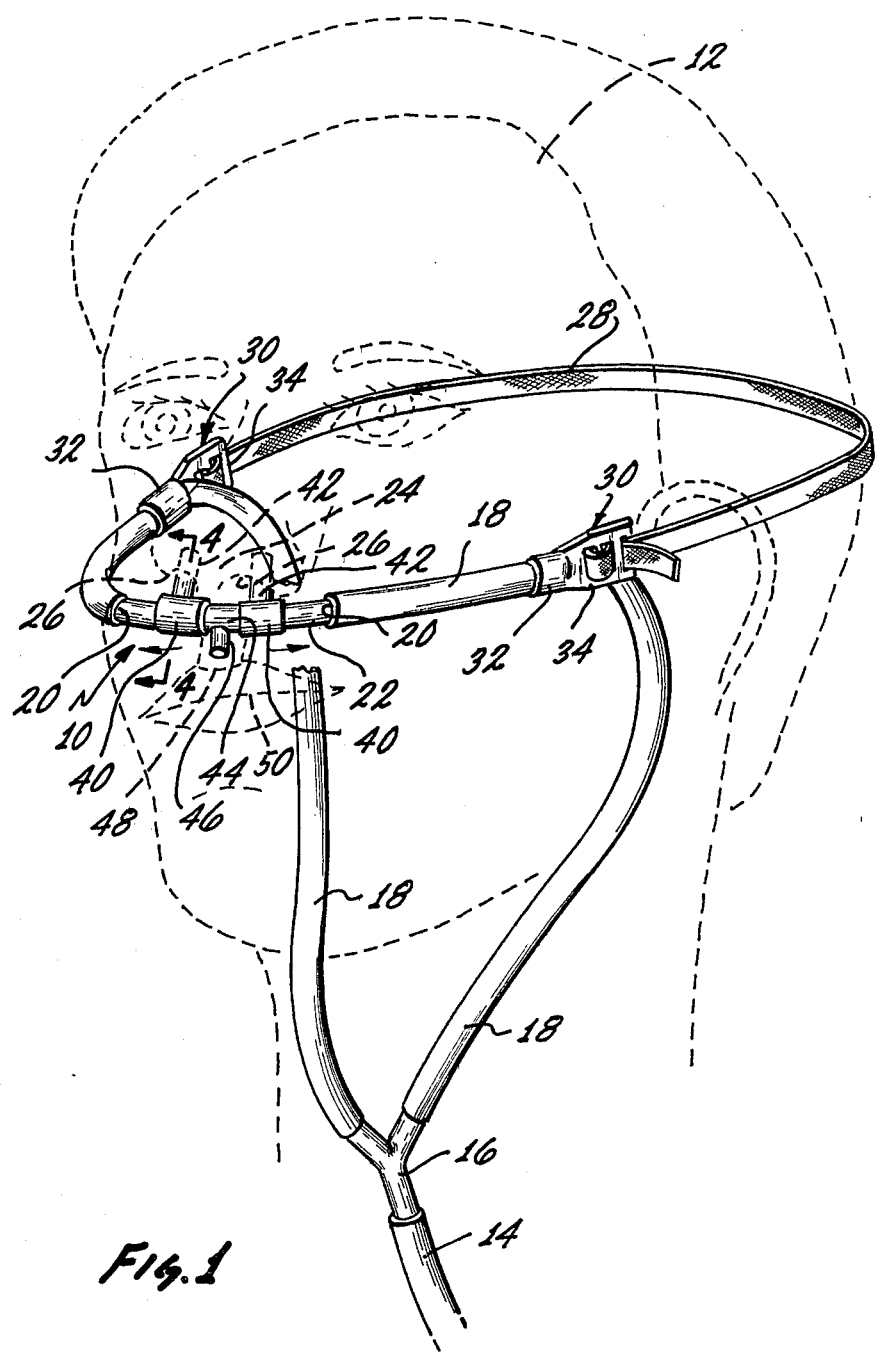
FIG. 1 is a view illustrating the use of a presently preferred embodiment or form of a nasal cannula structure of the present invention.

The illustrated nasal cannula structure is constructed so as to utilize the operative concepts or principles set forth and defined in the appended claims forming a part of this specification. These concepts or principles may easily be embodied within a number of differently appearing and somewhat differently constructed nasal cannula structures through the use or exercise of routine design skill on the basis of the disclosure embodied within this specification.

DETAILED DESCRIPTION

In the drawings there is shown a nasal cannula structure 10 of the present invention which is adapted to be utilized on the head 12 of an individual user. In the drawing this head 12 is shown by phantom lines merely for the purpose of illustrating how the structure 10 fits with respect to it. The structure 10 is adapted to receive a gas such as for example, oxygen, through a conventional flexible supply line or conduit 14 such as a rubber or similar polymer, somewhat resilient tube. This conduit 14 leads to a conventional rigid Y-fitting 16 forming a part of the structure 10. This Y-fitting 16 is secured to the lines 14 by friction; it concurrently supplies the gas received from the conduit 14 to two lateral lines or conduits 18 of a composition such as is employed in the line 14.

These in turn are utilized to supply the gas from the line 14 to the ends 20 of a centrally located elongated tubular conduit 22. Preferably this conduit 22 is formed of a rigid material; it is secured to the lines 18 by friction. With this structure the interior of the conduit 22 is located so as to receive a gas originally supplied by the conduit 14 through either of the lateral lines 18. This is considered to be quite desirable in case one of the lines 18 should for one reason or another be blocked off, as, for example as a result of this line 18 being flexible and being deformed as a result of a person laying on it.

The conduit 22 is adapted to be held generally parallel to the lower part (not separately numbered) of the nose 24 on the head 12 so as to be immediately adjacent to the nostrils 26 in the nose 24. An elastic band 28 is preferably utilized for the purpose of holding this conduit 22 in this position. This band 28 is adjustably connected to two different holders 30. Each of these holders 30 is located on one of the conduits 18.

Each of the holders 30 includes a band 32 fitting around a conduit 18 so as to be in frictional engagement with it, and a tab 34 attached to the band 32 so as to extend generally along a conduit 18. The band 28 is secured to each tab 34 by being threaded in and out of openings 36 in a conventional manner. With this type of structure the tension on the band 28 may be varied as desired in accordance with the size of the head 12 by the simple expedient of moving the band 28 relative to the tab 34 and the openings 36 in a conventional manner.

It of course will be obvious that the band 28 may be secured to the conduits 18 in other different manners, or that this band 28 may be secured directly to exposed portions of the conduit 22 if for one reason or another this is considered to be more convenient. This band 28 is essentially merely a support means for supporting the conduit 22 so that it extends in a position as indicated relative to a nose 24. It is immaterial as to whether or not the band 28 is directly connected to the conduit 22 in serving this function or whether it is indirectly secured to it as shown by being first connected to the lateral lines 18 which in turn are connected to the conduit 22. This band 28 is of such a nature that it can easily be moved relative to the head 12 in placing the structure 10 in an operative position or in removing it from a head 12.

The conduit 22 is preferably provided with two elongated, somewhat slot-like openings or holes 38 which are spaced from one another in an amount approximately corresponding to the spacing between the nostrils of the nose of the smallest head of an anticipated user of the structure 10. These holes 38 preferably extend long enough so as to approximate the distance or spacing between the nostrils of the nose on the largest head of an anticipated user. These holes 38 are preferably located so as to be aligned with one another along the shortest line extending between the ends 20 of the conduit 22. If the conduit 22 is slightly curved or bent—as in preferred—so as to approximately conform to the curvature of the face of an average user adjacent to and immediately beneath the nose 24, these holes 38 are preferably located adjacent to and immediately off to one side of the smallest internal radius of curvature employed in connection with such a bent conduit or tube.

Two separate sleeves 40 of rubber or of a polymer having resilient properties are located around the conduit 22. These sleeves 40 are sufficiently long so that each of them more than covers one of the holes 38. These sleeves 40 preferably fit with respect to the conduit 22 so that there is no danger of gas leakage generally between a sleeve 40 and the conduit 22. Further, these sleeves 40 preferably fit resiliently with respect to the conduit 22 in such a manner that their positions relative to the conduit 22 may be adjusted as required during the use of the structure 10. If desired, a small amount of petroleum jelly may be located around the conduit 22 to facilitate such adjustment.

Such adjustment is used so as to locate small tubes 42 on and preferably forming a part of the sleeves 40 so that these tubes 42 extend generally parallel to one another in a radially outward manner from the sleeves 40 into the nostrils 26 of the nose 24 in order to provide for gas flow through these tubes 42 into and/or out of the conduit 22. In all positions in which the tubes 42 may be used in connection with individuals having different nostril spacings, these tubes 42 will be in communication with the holes 38 in the conduit 22. In order to promote the comfort of a user, preferably these tubes 42 will be sufficiently thin so as to be slightly flexible and pliant.

These tubes 42 are preferably slightly smaller in dimension than the interiors (not separately numbered) of the nostrils 26 so as to fit comparatively loosely within these nostrils 26 in such a manner as to accommodate gas flow during breathing generally around the exteriors (not separately numbered) of the tubes 42. If desired, however, these tubes 42 may be shaped so as to fit closely within the interiors of the nostrils 26 in order to substantially eliminate any flow around them as the structure 10 is used. If desired, extending flanges or shields (not shown) can be located on the exteriors of the tubes 42 so as to fit against the nose 24 in order to effectively close off the nostrils 26 around these tubes 42.

As an aid to the location of the structure 10 in its desired position it is possible to include within the structure 10 a positioning sleeve 44 reasonably corresponding to the sleeves 40 of rubber or another somewhat pliant, resilient polymer material. When used this sleeve 44 will be midway between the sleeves 40 and will be held in place by frictional engagement with the conduit 22. It carries a projecting, somewhat pliant, flexible rod 46 which is adapted to fit generally against the head 12 as indicated in FIG. 1 within a comparatively small depression 48 extending generally between the nose 24 and the mouth 50. Because of the tension applied by the band 28 this rod 46 will serve to stabilize the structure 10 against shifting such as might tend to interfere with the structure 10 being held in a desired, operative location.

It is believed it will be apparent to those familiar with the use of nasal cannulas that the particular structure 10 described in the preceding is advantageous. It can be used with the lines 18 extending downwardly along the face in roughly the area of the temporomandibular joints or can be used with the lines 18 extending downwardly in back of the ears. It is preferred to utilize the structure 10 in the initial of these two manners in those cases where the resistance to gas flow caused by the internal dimensions of the lines 18 may be important or significant. It is considered one of the major advantages of the present invention lies in the fact that all of the internal passages within the structure 10 can be of relatively large dimension. This tends to lessen the pressure drop resulting from fluid flow through these passages. This can be quite significant in certain uses of the structure 10.

I claim:

1. A nasal cannula structure utilizing an elongated tubular conduit in which the improvement comprises:
    support means for supporting said conduit so that a portion of said conduit extends beneath and adjacent to the nostrils of the nose of a user,
    two separate, spaced holes located in said portion of said conduit said holes being separated from one another by an amount approximately corresponding to the spacing between the nostrils of the nose of a user,
    two separate sleeves located around said portion of said conduit, each of said sleeves covering one of said holes,
    a tube capable of fitting into a nostril of a user attached to each of said sleeves so as to extend outwardly from its, said sleeves each including means communicating with said tube so as to establish flow communication between said sleeve and said tube, said sleeves fitting closely against the exterior of said conduit so as to prevent gas leakage between the exterior of said conduit and the interiors of said sleeves, said sleeves also fitting against the exterior of said conduit in such a manner as to permit the relative locations of said sleeves with respect to said conduit to be adjusted so that said tubes fit within the nostrils of the nose of the user when said tubes are in communication with said holes.

2. A nasal cannula structure as claimed in claim 1 wherein:

said conduit is an elongated conduit having open ends, said structure includes two flexible tubes having connected ends, the other end of one of said tubes being connected to one end of said conduit, the other end of the other of said tubes being connected to the other end of said conduit.

3. A nasal cannula structure as claimed in claim 2 wherein:

said support means comprises an elastic band adapted to extend around the head of the usuer of said cannula, said band serving to hold said conduit so that said conduit extends between the mouth and the nose of such a user generally adjacent to the nostrils of the nose of the user.

4. A nasal cannula structure as claimed in claim 1 wherein:

said holes are shaped as elongated aligned slots having adjacent ends which are spaced from one another in an amount approximately corresponding to the spacing between the nostrils of the nose of the smallest head of an anticipated user and which extend long enough so as to approximate the spacing between the nostrils of the nose on the largest head of an anticipated user.

5. A nasal cannula structure as claimed in claim 1 wherein:

said structure includes a positioning means for facilitating said cannula structure being held in position relative to the head of a user, said positioning means including a sleeve fitting around said conduit between said holes, said sleeve carrying an extended rod which is adapted to fit against the head within a depression extending generally between the nose and the mouth.

6. A nasal cannula structure as claimed in claim 1 wherein:

said conduit is a rigid conduit, and said sleeves are formed of a resilient material and resiliently engage the exterior of said conduit, said tubes are integral with said sleeves and are flexible so as to be capable of deforming within the interior of the nostrils.

7. A nasal cannula structure as claimed in claim 1 wherein:

said conduit is an elongated rigid conduit having open ends, said holes are shaped as elongated slots having adjacent ends which are spaced from one another in an amount approximately corresponding to the spacing between the nostrils of the nose of the smallest head of an anticipated user and which extend long enough so as to approximate the spacing between the nostrils of the nose on the largest head of an anticipated user, said sleeves are formed of a resilient material and resiliently engage the exterior of said conduit, said tubes are integral with said sleeves and are flexible so as to be capable of deforming within the interior of the nostrils, said structure includes a positioning means for facilitating said cannula structure being held in position relative to the head of a user, said positioning means including a sleeve fitting around said conduit between said holes, said sleeve carrying an extended rod which is adapted to fit against the head within a depression extending generally between the nose and the mouth, said positioning means comprises a unitary body of a resilient material, said support means comprises an elastic band adapted to extend around the head of the usuer of said cannula, said band serving to hold said conduit so that said conduit extends between the mouth and the nose of such a user generally adjacent to the nostrils of the nose of the user.

* * * * *